United States Patent
Åkerblom

(10) Patent No.: US 6,610,666 B1
(45) Date of Patent: Aug. 26, 2003

(54) HYALURONAN PRODUCT AND PROCESS FOR MANUFACTURING THEREOF

(75) Inventor: Jim Åkerblom, Uppsala (SE)

(73) Assignee: Bio-Hyos AB, Uppsala (SE)

( * ) Notice: Subject to any disclaimer, the term of this patent is extended or adjusted under 35 U.S.C. 154(b) by 115 days.

(21) Appl. No.: 09/707,904

(22) Filed: Nov. 8, 2000

Related U.S. Application Data

(60) Provisional application No. 60/164,154, filed on Nov. 8, 1999.

(51) Int. Cl.[7] .................. A61K 31/175; C07N 1/08; C07N 7/033
(52) U.S. Cl. ................. 514/54; 536/123.1; 536/124; 536/127
(58) Field of Search ................ 514/54; 536/124, 536/123.1, 127

(56) References Cited

U.S. PATENT DOCUMENTS

| 4,141,973 A | 2/1979 | Balazs |
|---|---|---|
| 5,681,825 A | 10/1997 | Lindqvist et al. |
| 6,090,596 A | * 7/2000 | Stahl .................. 435/101 |

FOREIGN PATENT DOCUMENTS

| EP | 0 320 164 | 6/1989 |
|---|---|---|
| EP | 0 875 248 A1 | 11/1998 |
| GB | 2 172 295 A | 9/1986 |

* cited by examiner

*Primary Examiner*—Peter O'Sullivan
(74) *Attorney, Agent, or Firm*—Browdy and Neimark, P.L.L.C.

(57) ABSTRACT

This invention relates to a chemically unmodified hyaluronan product which has a high molecular weight of 9-25 million Daltons and a zero shear viscosity from 0.1 to 30 billion mPa s. This unique product is durable and at the same time viscoelastic, and perfectly compatible within the biocompatible materials, for instance, as a cartilage substitute and as an intervertebral disc. The invention also relates to a process for manufacturing of said product.

15 Claims, No Drawings

HYALURONAN PRODUCT AND PROCESS FOR MANUFACTURING THEREOF

This application claims the benefit of Provisional U.S. application Ser. No. 60/164,154, filed Nov. 8, 1999.

FIELD OF THE INVENTION

This invention relates to a chemically unmodified hyaluronan product which has enormously high molecular weight and extremely high viscosity i.e. zero shear viscosity. This unique product is durable and at the same time viscoelastic, and perfectly compatible within the biocompatible materials, for instance, as a cartilage substitute and as a intervertebral disc. The invention also relates to a process for manufacturing of said product.

BACKGROUND OF THE INVENTION

Hyaluronan (hyaluronic acid) is a naturally occurring polysaccharide which was first isolated in 1934 and 24 years later the structure of the molecule was totally defined. The first commerical product (Healon, trademark) was launched in 1980 within eye surgery, a product which is chemically unmodified. Since that time many similar product have been launched, some of them consist of only hyaluronan, with different molecular weight, from 0.5 to 8.0 million (Dalton) sterilized solution as described in the literature.

Most product are however, chemically modified hyaluronan, i.e. an extra chemical substance is added to the original hyaluronan molecule, to achieve higher viscoelastic properties, but it is always associated with risky side-effects. The cross-linked hyaluronan is known since 1963 (T. C. Laurent et al). A further drawback of cross-linked hyaluronan is the relatively short residence time in human tissues.

The chemical structure of hyaluronan is independent of origin in that hyaluronan is a linear polysaccharide without branching. The polysaccharide consists of a repeating disaccaharide unit of N-acetyl-D-glucosamino and glucuronate linked by $\beta(1\rightarrow3)$ and $\beta(1\rightarrow4)$ glycosidic bonds. It is well known that hyaluronan molecule in solution adopts a conformation of a stiffened random coil. Hyaluronan is produced by an enzyme complex in cell membranes. The enzymes produce hyaluronan from intracellular constituents, and the polysaccharide is directly extruded to the extracellular space.

The product of hyaluronan may be based on bacterial synthesis or on extraction from biological sources such as umbilical cord and rooster combs. The molecular weight of the isolated material depends, inter alia, on the quality of the raw material and the methods used for leaching, extraction, purification, sterilisation and the quality system. Strains of certain Streptococcus bacteria are capable of producing hyaluronan with molecular weights lower than leaching and extraction from rooster combs.

Hyaluronan produced by bacteria has to be cross-linked to achieve the higher molecular weight (i.e. zero shear viscosity) products required within the medical field.

To avoid the drawbacks with a chemically modified substance an unmodified hyaluronan product with high molelcular weight (i.e. zero shear viscosity) is infinitely preferable.

SUMMARY OF THE INVENTION

The present invention provides chemically unmodified hyaluronan with greatly improved molecular weight (i.e. zero shear viscosity) and with multiple applications within the medical field.

This inventin has been made possible through observing many previously unknown quality parameters plus the application of new technology with a combination of many steps from treatment of the naturally occurring raw material to the sterile end product. The process according to the invention is very rapid and takes at the most 1½ day to perform.

The process for production of hyluronan products gives according to the invention sterile products with zero shear viscosity from 5 million to 30 billion mPa s, which is totally unique. Due to the incredibly high shear vicosity it is possible to create various biocompatible products to be used in human beings and animals.

According to the present invention, greatly improved molecular weights are obtained and with suitable concentration, a product with specific viscoelastic properties can be created. Within the molecular weight range of 9–25 million Daltons and the concentration range of 10–39 mg/ml zero shear viscosity (from 5 million to 30 billion mPa s) is achieved according to the invention with a shear rate of 0.001 Hz.

Viscoelastic behaviour

The connection between zero shear viscosity and molecular weight and concentration is well known, see the equation below.

$$\text{Zero shear viscosity} = 5.3 \times 10^{26} \times (\text{concentration} \times M_r)^{3.643} \text{ (unit=Pa s)}$$

To produce viscoelastic substances with high zero shear viscosity, the only parameters that can be altered to create these products are molecular weight and concentration.

Note that, the parameter concentration is a strongly limiting factor. The colloid osmotic pressure of hyaluronan is of interest in conjunction with the use of hyaluronan substance in various body compartments. The colloid osmotic pressure is dependent on the number of molecular in solution and is thus a function of the number average molecular weight rather than the weight average molecular weight.

To arrive at an end product within the range of 9–25 million Dalton is extremely difficult, technically demanding and complicated. The patent application comprises a unique manufacturing system of sterile end products, whose vast medical significance is revolutionary for important clinical applications such as eye lenses, intervertebral discs, prostheses, etc Hyaluronan (hyaluronic acid) has physical properties with a broad range of medical applications; in othopedics, rheumatology, ophthalmology, dermatology, plastic surgery, otology, rhinology, neurology, urology, cardiothoracic surgery, adhesion prevention.

DETAILED DESCRIPTION OF THE INVENTION

Below a non-limiting example of the process of the invention will be described.

I. Process for the manufacturing of extremely high molecular weight hyaluronan

Raw material

As raw material especially roosters from the *White Leghorn* breed are used. They are genotypically and phenotypically selected within the molecular weight range of 10–50 million Daltons.

Extraction of water and salts and the reduction of microorganisms

Immediately after the combs are removed they are treated with 70% ethanol, proportion 1:5. Special equipment cleans the combs of biological impurities and this treatment is repeated 3–5 times with fresh ethanol. A diluted sodium phosphate solution can alternatively be added for the second step.

Pre-treatment of the combs

The combs are directly frozen to about −15 degrees Celsius sliced into extremely thin sections 0.001–0.1 mm thick, then rapidly frozen to −22 degrees Celsius in a freezing tunnel. Alternatively the combs can be ground into different particle sizes, instead of being sliced.

Leaching of hyaluronan under nitrogen atmosphere

In a diluted solution (0.5–2% NaCl solution) hyaluronan is leached from the material in up to seven steps, within nitrogen atmosphere. The leaching time varies from 3 minutes to 3 hours.

Removal of impurities under nitrogen atmosphere

The solution is treated with adsorptive media such as hydroxyapatite in one or several steps during gentle stirring and then filtrated.

Concentration of hyaluronan

The solution is concentrated for example through dialysis (PEG 3000)under vacuum conditions.

Packing and sterilisation of the hyaluronan product

With regard to molecular weight and concentration, different products are manufactured and packed into various types of dispensers. The product can be sterilised through radiation (16–28 kg Gray). Alternatively microwaves (10–300 W, 2450 Hz) or by autoclaving or sterile filtration of a diluted solution under acceptable conditions.

II. Medical application of the hyaluronan product

Based on the process of the invention four (A–D) separate intervals have been chosen for different medical applications with regard to rheological and chemical-physiological properties. Below an example in each category will be described.

EXAMPLE A

Hyaluronan Product for Eye Surgery

Products within range A, which have a zero shear viscosity between 100 million and 1 billion mPa s can characterised as having a high grade of extended "jellyness" with unique viscoelastic properties. When blinking very high shear rates occur so that the tear fluid must have a high zero shear viscosity to manage the huge shear rate. This happens at a low concentration with high molecular weight in order to provide good viscoelastic properties. Product A fulfils these properties.

EXAMPLE B

Hyaluronan Product as a Transplant Aid

Products within range B, which have a zero shear viscosity between 1 and 10 billion mPa s can be characterised as a "rubber ball" withstanding very high pressure while rotating within its own axis for a long period of time. Products within this range are suitable as transport substances for transplanting of e.g. insulin producing beta-cells. By transplanting beta-cells in the hyaluronan random coil configuration, mechanisms of rejection are avoided. The beta-cells continue to be vigorous in hyaluronan and can continue to produce insulin. Product B contains these properties.

EXAMPLE C

Hyaluronan Product as a Muscle Support

Products within range C, which have a zero shear viscosity between 10 and 20 billion mPa s can be characterised as having a constant viscoelastic property, independent of time. An application which demands high zero shear viscosity is incontinence, where the substance must be as viscoelastic as a rubber ball in order to support weak tissue and failing musculature. Product C contains these properties.

EXAMPLE D

Hyaluronan Product as a Cartliage and Bone Substitute

Products within range D having a zero shear viscosity between 20 and 30 billion mPa s can be characterised as having a solid substance which is not degradable, containing a unique function of both viscous and elastic behaviour. With increasing molecular weight the inter-chain interaction stabilises the molecule through its double helix structure in hyaluronan macro-molecules, i.e. with extremely high molecular weight the molecule works as an internal cross-linked macro-molecule.

The product range D can be used as cartilage substitute and at the upper tolerance limit as a substitute for damaged discs (intervertebral disc). The hyaluronan product remains as a very thin film between the bones even at extremely high pressures in luxations or damaged cartilage in the joints.

Degree of purity

The products according to the present invention have a degree of purity which is more than a 30% improvement upon Healon (trademark) with regard to endotoxin EU/ml. A sterile hyaluronan solution according to the invention has the following characteristics:

a protein content below 100 ug/g;
 an absorbance of a 1% solution at 257 nm of at the most 1.5 and at 280 nm of at the most 1.5;
 an iron content of at the most 0.1mg/g;
 a cooper content of at the most 0.1mg/g;
 an acetone content of at the most 2mg/g;
 a ethanol content of at the most 6mg/g;
 an endotoxin content of at the most Limulus 0.35 EU endotoxin/ml;
 a pH value from 7.0 to 7.5

Preferably the hyaluronic acid according to the invention is in the form of its sodium salt. The hyaluronic acid solution is buffered in a physiologically acceptable buffer.

What is claimed is:

1. A sterile chemically unmodified hyaluronan product in which the hyaluronan has a molecular weight of 9–25 million Daltons and a concentration of 10–39 mg/ml, said product having zero shear viscosity from 0.1 to 30 billion mPa s.

2. A product according to claim 1, wherein the zero shear viscosity is 0.1–1.0 billion mPa s.

3. A product according to claim 1, wherein the zero shear viscosity is 1.0–10 billion mPa s.

4. A product according to claim 1, wherein the zero shear viscosity is 10–20 billion mPa s.

5. A product according to claim 1, wherein the zero shear viscosity is 20–30 billion mPa s.

6. A process for manufacturing of a high molecular weight hyaluronan product by
 extracting from rooster combs, wherein the rooster combs are genotypically and phenotypically selected from rooster combs comprising hyaluronate within the molecular weight range of 10–50 million Dalton,
 and processing said rooster combs to produce a hyaluronan having a shear viscosity greater than 0.1 billion mPa s.

7. A process according to claim 6, comprising the following steps after selection of rooster combs, extraction of water and salts and reduction of microorganisms;

pre-treatment of the combs by freezing and disrupting the combs;

leaching of hyaluronan;

removal of impurities;

concentration of hyaluronan; and packing and sterilisation of the hyaluronan product.

8. A process according fo claim 6, wherein the rooster combs are derived from the species *White Leghorn*.

9. A process according to claim 7, wherein the rooster combs are derived from the species *White Leghorn*.

10. In a method of using hyaluronan in medical or surgical procedure, the improvement wherein said hyaluronan is the product of claim 1.

11. The method of claim 10, wherein said procedure comprises implanting said product into a human patient.

12. The method of claim 11, wherein said implanting is for eye surgery, muscle support, cartilage substitution or bone substitution.

13. The method of claim 10, wherein the zero shear viscosity of said product is 20–30 billion mPa s.

14. The method of claim 10, wherein said product is obtained from rooster combs.

15. A sterile chemically unmodified hyaluronan product in which the hyaluronan has a molecular weight of 9–25 million Daltons, a concentration of 10–39 mg/ml and a zero shear viscosity from 0.1 to 30 billion mPa s, said product being an extract of rooster combs comprising hyaluronate within the molecular range of 10–50 million Dalton.

* * * * *